(12) United States Patent
Na et al.

(10) Patent No.: US 9,709,561 B2
(45) Date of Patent: Jul. 18, 2017

(54) MULTISENSING PLATFORM HAVING A NANOPOROUS METAL LAYER ON A CANTILEVER SENSOR

(71) Applicants: KOREA UNIVERSITY RESEARCH AND BUSINESS FOUNDATION, Seoul (KR); INDUSTRY-ACADEMIC COOPERATION FOUNDATION, YONSEI UNIVERSITY, Seoul (KR)

(72) Inventors: Sung Soo Na, Seoul (KR); Jinsung Park, Seoul (KR); Seungjoo Haam, Seoul (KR); Doyeon Bang, Seoul (KR)

(73) Assignees: KOREA UNIVERSITY RESEARCH AND BUSINESS FOUNDATION, Seoul (KR); INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 96 days.

(21) Appl. No.: 14/525,970

(22) Filed: Dec. 10, 2014

(65) Prior Publication Data
US 2015/0330977 A1    Nov. 19, 2015

(30) Foreign Application Priority Data
May 13, 2014  (KR) .................. 10-2014-0057276

(51) Int. Cl.
*G01N 33/553*  (2006.01)
*G01N 21/65*  (2006.01)
(Continued)

(52) U.S. Cl.
CPC ......... *G01N 33/54373* (2013.01); *B82B 1/00* (2013.01); *C23F 1/00* (2013.01);
(Continued)

(58) Field of Classification Search
CPC ........ G01N 33/54; G01N 21/65; G01N 33/55; G01N 21/653
(Continued)

(56) References Cited

U.S. PATENT DOCUMENTS 5,445,008 A * 8/1995 Wachter ............... G01N 29/036
                                                                422/88
6,457,360 B1 * 10/2002 Daraktchiev ......... B81B 3/0018
                                                                73/504.15
(Continued)

FOREIGN PATENT DOCUMENTS

JP       2007-121306       5/2007
KR     1008926200000      4/2009
(Continued)

OTHER PUBLICATIONS

Fagan, B. C. et al, Talanta 2000, 53, 599-608.*
(Continued)

*Primary Examiner* — Arlen Soderquist
(74) *Attorney, Agent, or Firm* — Duane Morris LLP; J. Rodman Steele, Jr.; Gregory M. Lefkowitz

(57) ABSTRACT

Provided is a nanoporous cantilever including a substrate in a shape of a plate, a tip formed at a front end of the substrate, and a nanoporous structure formed on the tip. Due to the nanoporous structure including nanopores and nanochannels formed on the tip, the nanoporous cantilever greatly increases in detection sensitivity for a material to be detected when compared to a cantilever according to a related art, and may obtain a surface-enhanced Raman signal and thus achieve discrimination of a molecule to be detected.

14 Claims, 7 Drawing Sheets

FIG. 2

(51) Int. Cl.
*G01N 33/543* (2006.01)
*G01N 29/036* (2006.01)
*C23F 1/00* (2006.01)
*G01N 29/02* (2006.01)
*B82B 1/00* (2006.01)
*G01G 3/16* (2006.01)
*B82Y 15/00* (2011.01)
*G01N 15/00* (2006.01)

(52) U.S. Cl.
CPC ............ *G01G 3/165* (2013.01); *G01N 21/65* (2013.01); *G01N 21/658* (2013.01); *G01N 29/022* (2013.01); *G01N 29/036* (2013.01); *B82Y 15/00* (2013.01); *G01N 2015/0038* (2013.01); *G01N 2201/06113* (2013.01); *G01N 2291/023* (2013.01); *Y10S 977/954* (2013.01); *Y10S 977/958* (2013.01); *Y10T 428/24997* (2015.04); *Y10T 428/249953* (2015.04)

(58) Field of Classification Search
USPC ................ 422/69; 436/86–87, 164, 171, 172
See application file for complete search history.

(56) References Cited

U.S. PATENT DOCUMENTS

| | | | | |
|---|---|---|---|---|
| 7,105,301 | B2* | 9/2006 | Su | C12Q 1/6825 435/5 |
| 7,694,346 | B2* | 4/2010 | Adams | G01N 29/036 250/234 |
| 8,349,611 | B2* | 1/2013 | Loverich | G01N 29/022 422/82.01 |
| 8,652,632 | B2* | 2/2014 | Demirel | B05D 1/60 427/255.6 |
| 8,904,850 | B1* | 12/2014 | Allendorf | G01N 29/022 310/313 B |
| 2005/0084912 | A1* | 4/2005 | Poponin | B82Y 20/00 435/7.1 |
| 2012/0077057 | A1* | 3/2012 | Kysar | C23C 26/00 428/613 |
| 2013/0032006 | A1* | 2/2013 | Detsi | G01N 19/10 75/330 |
| 2013/0118228 | A1* | 5/2013 | Parpia | G01N 33/497 73/23.3 |

FOREIGN PATENT DOCUMENTS

| | | |
|---|---|---|
| KR | 1020090034602 | 4/2009 |
| KR | 1009994240000 | 12/2010 |
| KR | 1020110056073 | 5/2011 |
| KR | 1010536550000 | 7/2011 |
| KR | 1011035780000 | 1/2012 |
| KR | 1011137930000 | 2/2012 |

OTHER PUBLICATIONS

Lavrik, N. V. et al, SPIE 2001, 4560, 152-161.*
Kramer, D. et al, Nano Letters 2004, 4, 793-796.*
Choudhury, A. et al, Journal of Micromechanics and Microengineering 2007, 17, 2065-2076.*
Singamaneni, S. et al, Advanced Materials 2008, 20, 653-680.*
Allendorf, M. A. et al, Journal of the American Chemical Society 2008, 130, 14404-14405.*
Duan, H., Acta Mechanica Solida Sinica 2010, 23, 1-12.*
Xu, P. et al, Analytical Chemistry 2011, 83, 3448-3454.*
Urbiztondo M. A. et al, Sensors and Actuators B: Chemical 2012, 171-172, 822-831.*
Li, R. et al, Physical Review Letters 1992, 68, 1168-1172.*
Erlebacher, J. et al, Nature 2001, 410, 450-453.*
Ding, Y. et al, Journal of the American Chemical Society 2003, 125, 7772-7773.*
Qian, L. H. et al, Applied Physics Letters 2007, 90, article 153120, 3 pages.*
Qian, L. H. et al, Applied Physics Letters 2007, 91, article 083105, 3 pages.*
Snyder, J. et al, Journal of The Electrochemical Society, 2008, 155, C464-C473.*
Chen, L.-Y. et al, Advanced Functional Materials 2009, 19, 1221-1226.*
Lang, X. Y. et al, Journal of Physical Chemistry C 2009, 113, 10956-10961.*
Xu, C. et al, Physical Chemistry Chemical Physics 2010, 12, 239-246.*
Kamundi, M. et al, Journal of Physical Chemistry C 2012, 116, 14123-14133.*
Qi, J. et al, Nanoscale, 2013, 5, 4105-4109.*

* cited by examiner

MULTISENSING PLATFORM HAVING A NANOPOROUS METAL LAYER ON A CANTILEVER SENSOR

CROSS-REFERENCE TO RELATED APPLICATIONS

This application claims priority under 35 U.S.C. §119 to Korean Patent Application No. 10-2014-0057276 filed on May 13, 2014 in the Korean Intellectual Property Office, the disclosure of which is incorporated herein by reference in its entirety.

TECHNICAL FIELD

The present disclosure relates to a multisensing platform using a nanoporous cantilever sensor, and more particularly, to a nanoporous cantilever which may discriminate a detected molecule with high sensitivity by combining a function of a resonance sensor of a cantilever and a surface-enhanced Raman scattering function of a nanostructure, and a multisensing platform with the same, and molecule detection using the same.

BACKGROUND

Over the past 20 years, there have been many developments of methods and apparatuses for sensing chemical materials, biochemical materials and environmental toxicity in the sensor field. Monitoring of chemical materials and biochemical materials is very important to not only medical diagnosis and bio-warfare applications but also to basic research.

Recently, the use of nanosized materials in the fields of industry or science is dramatically increasing. Such nanoparticles have higher reactivity than existing materials due to properties of a small size and a wide specific surface area, and their harmful influences on human bodies and environment have been reported through many studies. For this reason, attempts have been being made in many aspects to improve a detection range of nanosized toxic materials. A typical detection method includes labeling with a quantum dot, a fluorescent marker, a dye, and the like. This labeling detection method may be widely used in molecule detection but needs to consider photochemical decomposition, pH dependency, time limitation, high costs, and the like. To pursue a diverse range of targets and overcome the limitations of a labeling method, current technology development focuses on building a multimodal system to achieve sensitivity improvement, label-free detection, cost reduction and analytical molecule detection.

A cantilever sensor is a sensor which detects a fine material by applying a piezoelectric mechanism using a piezoelectric material, and is primarily manufactured through a micro electro mechanical system (MEMS) process. A microcantilever sensor is greatly classified into a microbalance principle and a surface stress principle in its application. The former is a dynamic mode that measures a change of resonant frequency with a change in mass and spring constant of a cantilever, and the latter is a static mode that measures strain with a change in surface stress by a specific reaction on a microcantilever. This microcantilever sensor features high sensitivity, high selectivity and label-ing-free detection, and may be used to analyze pathogen including DNA, marker proteins and small molecule biomaterials. However, because a cantilever sensor is a sensor responsive to a change in mass, there are drawbacks that even when an unwanted material is attached to the sensor surface, the cantilever sensor responds thereto and the cantilever sensor cannot identify a detected molecule.

A surface-enhanced Raman scattering (SERS) sensor is a new concept of Raman sensor that overcomes low reactivity noted as a drawback of a conventional Raman sensor by amplifying a reactivity value of a Raman sensor using a nanostructure or nanoparticles, and has an advantage of discriminating a detected chemical molecule through signal analysis. However, to manufacture an SERS sensor, a complex nanostructure and various processes are needed, so it takes much time to manufacture and a manufacturing cost is high, resulting in low economic efficiency, and there are drawbacks of a lack of macro uniformity and a lack of compatibility with an MEMS.

RELATED LITERATURES

Patent Literature (Patent Literature 1) Korean Patent Publication No. 1,103,578

(Patent Literature 2) Korean Patent Publication No. 999,424

(Patent Literature 3) Korean Patent Publication No. 1,053,655

(Patent Literature 4) Korean Patent Publication No. 1,113,793

(Patent Literature 5) Korean Patent Application Publication No. 10-2009-0034602

(Patent Literature 6) Korean Patent Publication No. 892,629

SUMMARY

The present disclosure is directed to providing a multisensing platform-based nanoporous cantilever with a function of a resonance sensor and a function of a surface-enhanced Raman scattering (SERS) sensor to detect a molecule to be detected at low concentration with high sensitivity and identify a feature of the molecule to be detected.

Also, the present disclosure is directed to providing a method for manufacturing the nanoporous cantilever.

To address the above issue, there is provided a nanoporous cantilever including a substrate in a shape of a plate, a tip formed at a front end of the substrate, and a nanoporous structure formed on the tip.

According to an exemplary embodiment of the present disclosure, the nanoporous structure may be a structure in which a plurality of nanopores having an average diameter of 5 to 100 nm and a plurality of nanochannels having an average diameter of 50 to 1000 nm are connected to each other in three dimensions.

According to another exemplary embodiment of the present disclosure, the nanoporous structure may be made of any one metal or at least two metals selected from the group consisting of gold, silver, chrome, platinum, aluminum and copper.

According to another exemplary embodiment of the present disclosure, the nanoporous structure may have a thickness of 10 nm to 10 μm.

According to another exemplary embodiment of the present disclosure, the nanoporous cantilever may further include a piezo-electric resistance sensor.

According to another exemplary embodiment of the present disclosure, the nanoporous cantilever may emit a Raman scattering signal.

In another aspect, there is provided a method for manufacturing a nanoporous cantilever, including depositing a metal/silver alloy layer on a tip formed at a front end of a substrate, and forming a metal nanoporous structure on the tip by etching the metal/silver alloy layer to selectively remove silver.

According to another exemplary embodiment of the present disclosure, the metal may be at least one selected from gold, chrome, platinum, aluminum and copper.

According to another exemplary embodiment of the present disclosure, the metal/silver alloy layer may have a metal content of 1 to 70 at %. According to another exemplary embodiment of the present disclosure, the nanoporous structure may be a structure in which a plurality of nanopores having an average diameter of 5 to 100 nm and a plurality of nanochannels having an average diameter of 50 to 1000 nm are connected to each other in three dimensions.

In another aspect, there is provided a multisensor for detecting a material, including the nanoporous cantilever.

In another aspect, there is provided a method for detecting a material, including measuring a resonant frequency shift and a surface-enhanced Raman scattering signal simultaneously using the nanoporous cantilever.

According to another exemplary embodiment of the present disclosure, the material may be at least one selected from a chemical molecule, protein, an antibody, a virus, a bacteria, DNA, aptamer, and a low molecular biomolecule.

The nanoporous cantilever having a metal structure including a plurality of nanoporous structures made up of nanopores and nanochannels on a tip formed at a front end of a substrate according to the present disclosure has sensitivity for detection of a material to be detected 10,000 times higher than a cantilever according to a related art, and as it may obtain a Raman signal by the nanoporous structure, may facilitate analysis of a detected molecule.

DETAILED DESCRIPTION OF EMBODIMENTS

The present disclosure relates to a nanoporous cantilever which may detect a molecule to be detected at low concentration with high sensitivity and analyze a feature of the detected molecule by using a function of a resonance sensor of a cantilever and a function of a surface-enhanced Raman scattering (SERS) sensor together, and a method for manufacturing the same and a molecule detection method using the same Hereinafter, the present disclosure will be described in more detail.

Figure 1:
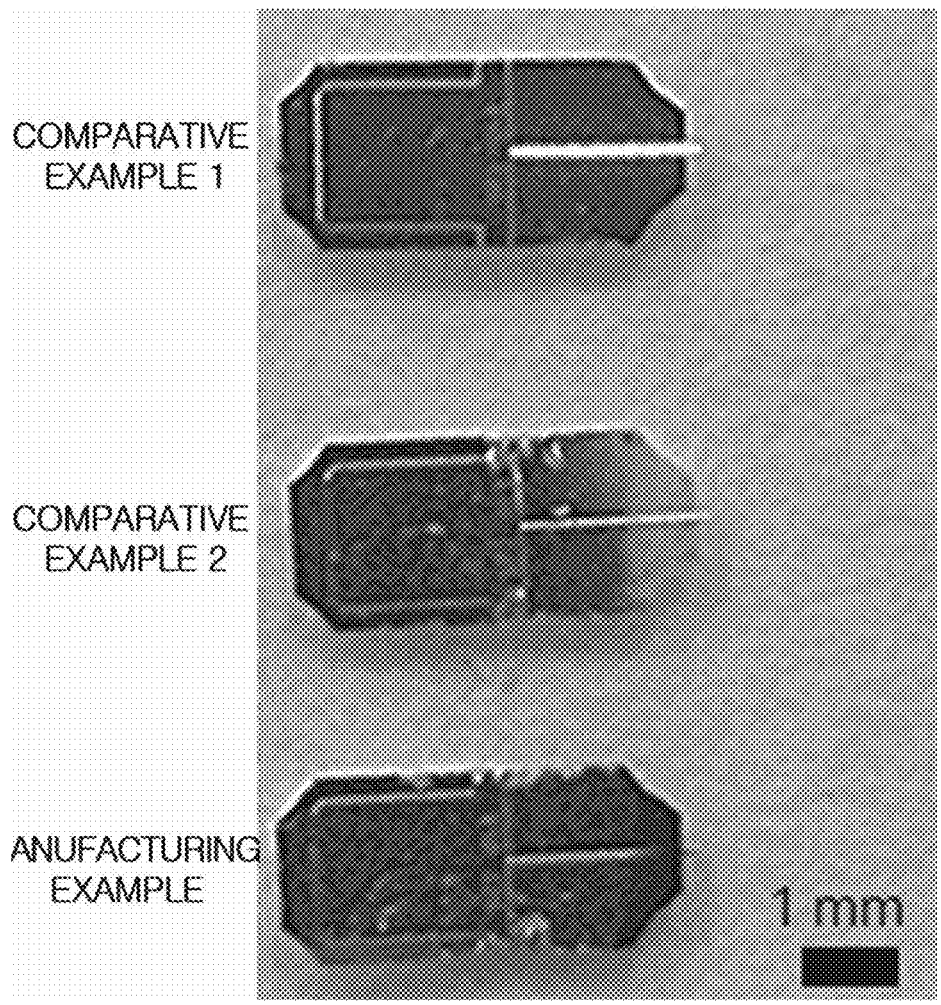
FIG. 1 shows an actual image of resonators according to Comparative example 1, Comparative example 2, and a manufacturing example of the present disclosure.
Figure 2:
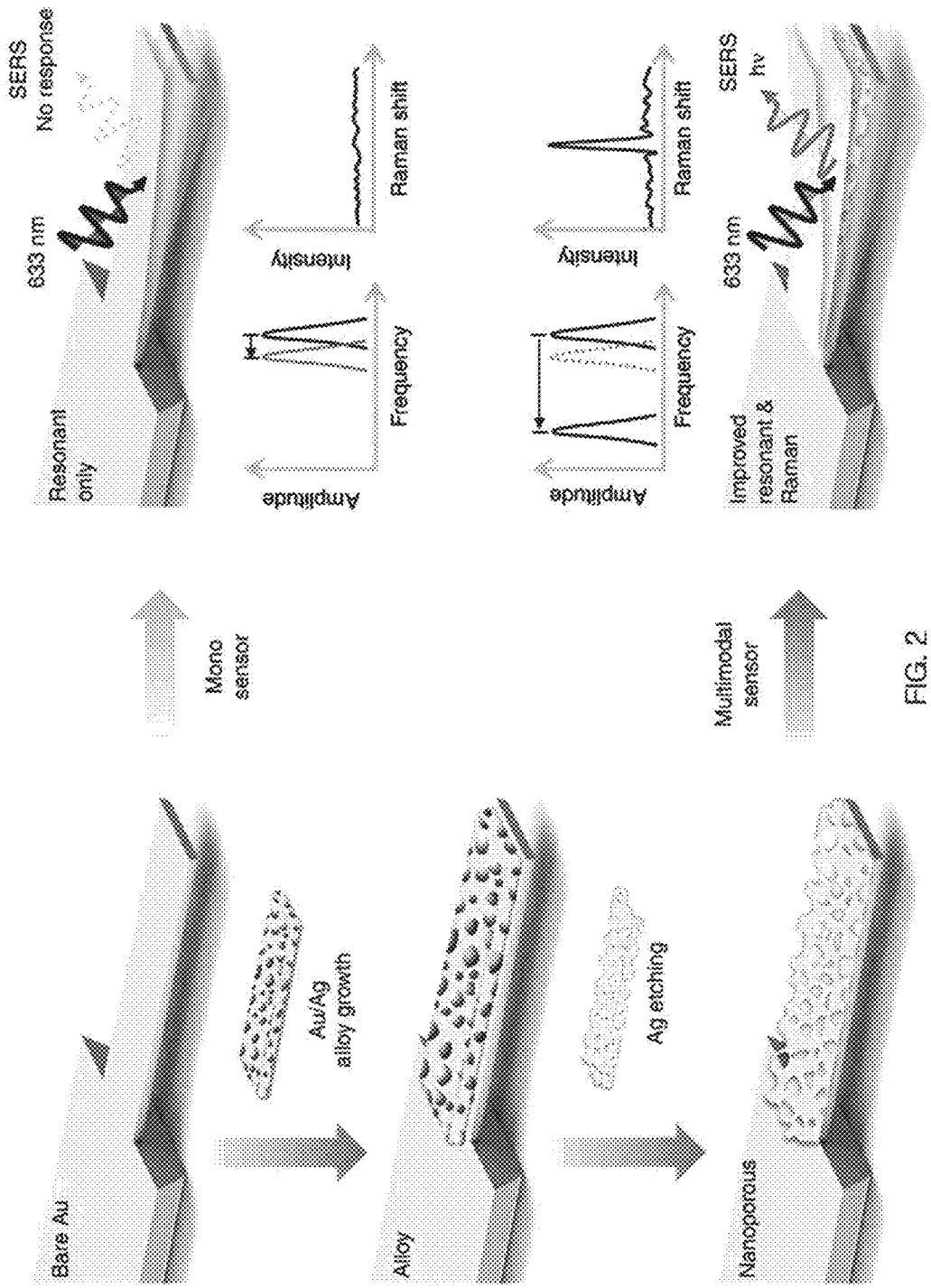
FIG. 2 is a conceptual diagram of a nanoporous cantilever according to the present disclosure.

FIG. 2 is a conceptual diagram of a nanoporous cantilever according to the present disclosure.

The nanoporous cantilever according to the present disclosure is characterized by including a plate-shaped substrate, a tip formed at a front end of the substrate, and a nanoporous structure formed on the tip.

The nanoporous structure formed on the tip according to the present disclosure may be a structure in which a plurality of nanopores having an average diameter of 5 to 100 nm and a plurality of nanochannels having an average diameter of 50 to 1,000 nm are connected in 3 dimensions.

The nanostructure may be made of any one metal or at least two metals selected from the group consisting of gold, silver, chrome, aluminum and copper, and preferably, the nanostructure may function to increase sensitivity for detection of a material to be analyzed by enhancing surface plasmon resonance and may serve as a hot spot upon surface-enhanced Raman scattering to strengthen an ambient electromagnetic field, thereby increasing sensitivity for detection of a material to be analyzed and discriminating a detected molecule.

The nanoporous structure formed on the tip according to the present disclosure may allow various adjustment of a size, a shape, a density and a thickness based on materials to be analyzed, and may allow various adjustment of a size and a gap of the nanopores and the nanochannels.

The sensitivity of the resonance sensor is proportional to a mass increase and an adsorption probability of a molecule, and when the nanoporous structure is formed on the tip according to the present disclosure, a surface area of the cantilever may be improved and an adsorption probability of a material to be analyzed may increase, so sensitivity of the resonance sensor may be greatly improved when compared to a cantilever without a nanoporous structure, thereby, preferably, ensuring the limit of detection at concentration lower than $10^{-9}$ M without the aid of an amplifier.

Particularly, when the nanostructure is made of gold, results were obtained that sensitivity as a resonance sensor is improved in comparison to a nanostructure made of other metal or two or more metals, and sensitivity for detection of a material to be analyzed is further improved.

The nanoporous cantilever according to the present disclosure may be manufactured by depositing a metal/silver alloy layer on a tip formed at a front end of a substrate, and forming a metal nanoporous structure on the tip by etching the metal/silver alloy layer to selectively remove silver.

The metal may be any one or at least two selected from gold, chrome, platinum, aluminum and copper.

According to the present disclosure, in particular, depositing a gold/silver alloy layer using gold as the metal is preferred because it is easier to selectively remove silver than depositing a metal/silver alloy layer using other metal, may allow a nanoporous structure connected in three dimensions to be formed due to favorable distribution of nanopores and nanochannels, and may manufacture a cantilever with high sensitivity for detection of a material to be analyzed and improved sensitivity as a resonance sensor.

The etching for selectively removing silver from the metal/silver alloy layer may be performed by treating with nitric acid for 2 to 5 seconds.

According to the manufacturing method of the present disclosure, the nanoporous cantilever with the nanoporous structure of metal may be manufactured by depositing the metal/silver alloy layer on the surface of the tip of the cantilever using an electrochemical deposition method, and etching silver using nitric acid in a quick and simple manner.

According to the present disclosure, the nanoporous structure may be formed on the tip by variously adjusting a size, a shape, a density, and a thickness based on materials to be analyzed.

The thickness of the nanoporous structure may be adjusted by adjusting a deposition thickness of the metal/silver alloy layer, and a preferred deposition thickness of the metal/silver alloy layer may be from 10 nm to 10 µm.

When the thickness of the metal/silver alloy layer is less than 10 nm, intensity of a surface-enhanced Raman signal obtained from the generated nanoporous structure is low, and when the thickness of the nanoporous structure exceeds the range, it is not preferred because unremoved silver may remain and a nanoporous structure not easy to develop nanopores and nanochannels may be generated.

According to the present disclosure, a density and a shape of the nanoporous structure and a size and a gap of the nanopores and the nanochannels may be adjusted by adjusting a metal content of the metal/silver alloy layer.

The metal content of the metal/silver alloy layer may be adjusted by preparing each of a metal plating stock solution and a silver plating stock solution and adjusting a mix ratio of the stock solutions.

According to the present disclosure, the metal content of the metal/silver alloy layer may be from 1 to 70 at %. Particularly, the use of gold as the metal and gold contents of 1 to 30 at % may allow a nanoporous structure with improved normalized surface area to be obtained due to favorable development of nanopores and nanochannels after silver etching. The nanoporous structure according to the present disclosure is preferred because an adsorption probability of a detected molecule may be improved to increase sensitivity of a resonance sensor, and a good surface-enhanced Raman signal may be obtained due to localized plasmon hot spots.

The detection method according to the present disclosure is characterized by using a change in mechanical property, to be exact, a change in resonant frequency following a mass change occurring when the detected molecule is attached to the surface, and detection of a Raman scattering signal.

The resonant frequency is a natural frequency that all objects have and has a relationship with a mass and a spring constant. Sensitivity of a resonance sensor is proportional to a mass increase and an adsorption probability of a molecule, and to increase the mass, sensitivity of a resonance sensor may be further increased using a sandwich technique which attaches a material capable of binding to a detected material one more time.

EXAMPLES

Manufacturing Example. Manufacture of Multimodal Nanoporous Resonator (MNPR)

To manufacture a multimodal nanoporous resonator, a PPP-NCHAu (NANOSENSORS, Switzerland) cantilever with a resonator having a force constant of 42 $Nm^{-1}$ was used, and a standard was 30×4×125 µm$^3$ (width×thickness×length). To improve a contact area, an Au coating layer was formed on both surfaces of the resonator. The resonant frequency of the resonator was about 240 kHz suitable to use a cantilever sensor in the air.

An electrochemical experiment was controlled using a computer, and measurement was performed using a potentiostat (CompactStat, Ivium). A 3 electrode system using a Pt wire counterelectrode, an Ag/AgCl (1M KCl) reference electrode, and a working electrode was used.

To identify the characteristics of the cantilever based on Au contents of an Au/Ag alloy layer, an Au/Ag alloy deposition solution was prepared by preparing each of an Au plating stock solution and an Ag plating stock solution and changing a mix ratio, and the Au/Ag alloy layer was deposited using an electrochemical deposition method. The Au/Ag alloy deposition solution was prepared with Au contents of 50, 25, 12.5, and 6.25 at % based on the total metal at %. Meanwhile, the Au plating stock solution and the Ag plating stock solution were prepared by dissolving 20 mM gold cyanide and 20 mM silver cyanide in an aqueous medium, respectively, and adjusting pH using $NaCO_3$.

The Au/Ag alloy layer was deposited by applying voltage of −0.8 V to Ag/AgCl for 180 seconds, and a reaction was performed in a container of which temperature was controlled to 10° C. The Au/Ag alloy layer-deposited cantilever was treated with nitric acid for 2 seconds to selectively remove (etch) silver from the Au/Ag alloy layer. After the selective etching, the cantilever was washed with ethanol and ultra pure water several times and vacuum dried for 6 hours at room temperature, to manufacture a multimodal nanoporous resonator (MNPR).

Comparative Example 1

Instead of the cantilever of the example, a resonator using a commercially available cantilever, a SSS-NCHR (NANOSENSORS, Switzerland) cantilever, coated with Au on the surface was used.

Comparative Example 2

A resonator using a cantilever in which an Au/Ag alloy layer was formed on a PPP-NCHAu cantilever was used.

Example 1. Resonator Characteristics Analysis

Example 1.1. Tapping Mode Atomic Force Microscope (tmAFM) Analysis

In the ambient temperature, pressure, and air, a tapping mode atomic force microscope (tmAFM) image was obtained using Innova (Bruker) with a nanodrive controller (Bruker). To obtain an accurate and reproducible tapping mode image, a closed-loop scanner was used, and to obtain a precision image, 2-dimensional (2D) and 3-dimensional (3D) images were obtained using an SSS-NCHR (NANOSENSORS, Switzerland) cantilever tip known as an ultra shape tip. The resonant frequency of the cantilever was about 300 kHz, and a tip radius was about 2 nm.

The size of all the images was standardized to 3×3 μm at a scanning frequency of 0.8 Hz. A 2D leveling process was performed on all the images using SPM Lab Analysis software V7.00 (Bruker), and surface area analysis was conducted using Nanoscope analysis software V1.20 (Bruker).

A normalized surface area may be represented by the following equation (1).

$$A_n = A_m / A_b \quad \text{Equation (1)}$$

In the above equation (1), $A_m$ denotes a surface area of Example 1, and $A_b$ denotes a surface area of Comparative example 1.

Example 1.2. Raman Spectroscopy Analysis

Raman spectroscopy was measured using a confocal Raman microscope LabRAM ARAMIS (Horiba). A high resolution image was obtained using A×100 microscope objective lens (Nikon, NA=0.95) and He—He laser (λ=633 nm). A laser power used to a detected molecule is about 50 μW, and an integration time is 10 seconds. A spectrometer was corrected using a silicon wiper having a Raman band of 520 cm$^{-1}$. In the case of a confocal Raman imaging spectrometer, a laser power used to a detected molecule was about 0.5 mW, an integration time was 1 sec per spectrum, a scanning mode was about 0.5 mW, and intensity of an SERS signal was mapped onto a 10×10 μm square range of a center neck site of a resonator. Also, a spectrum and an image was analyzed using LabSpec 5 software (Horiba).

Example 1.3. FE-SEM and EDS Analysis

To observe a resonator surface shape, FE-SEM and energy dispersive spectroscopy (EDS) measurement was performed. FE-SEM and EDS analysis was conducted using an energy dispersive X-ray FE-SEM (JSM-7100F, JEOL) at an acceleration voltage of 20 kV.

Example 1.4. Electrochemical Surface Analysis

For surface analysis, an electrochemical experiment was performed using a potentiostat (CompactStat, Ivium). Using a 3 electrode system using a Pt counterelectrode, an Ag/AgCl (1M KCl) reference electrode, and a working electrode, an experiment was carried out on the cantilevers according to Comparative example and Example. To measure the electrochemical active surface, a circulating current voltage curve in a potential range of 0.5 to 1.8 was measured at a scan rate of 10 mVs-1 in 0.5 M sulfuric acid solution. To improve reliability, the measurement was made 20 times, and for surface area estimation, integration of gold oxidation-reduction peaks in a range of 0.5 V to 1.5 V was performed.

Example 2. p-ATP Detection Comparison and Control Experiment

Using the resonators according to Example and Comparative example, a resonant frequency shift in response to adsorption of p-aminothiophenol (p-ATP) having an amine group and a thiol group at both ends was measured using an atomic force microscope (Innova) with a nanodrive controller. To facilitate the adsorption of p-ATP on the resonator surface according to Example and Comparative example, the resonators of Example and Comparative example was immersed for 1 hour in an ethanol buffer solution in which p-ATP was dissolved, and a well-known gold/sulfur compound was attached to the gold surface of the resonators of Example and Comparative example. As a control, the resonator was immersed in 100% ethanol and compared.

Referring to SEM and tmAFM images of FIGS. 3a through 3d, the surface of the resonator according to Comparative example 1 is smooth, while proper formation of a nanoporous structure in which nanopores and nanochannels are connected in three dimensions is observed from the resonator according to the manufacturing example.

Figure 3:
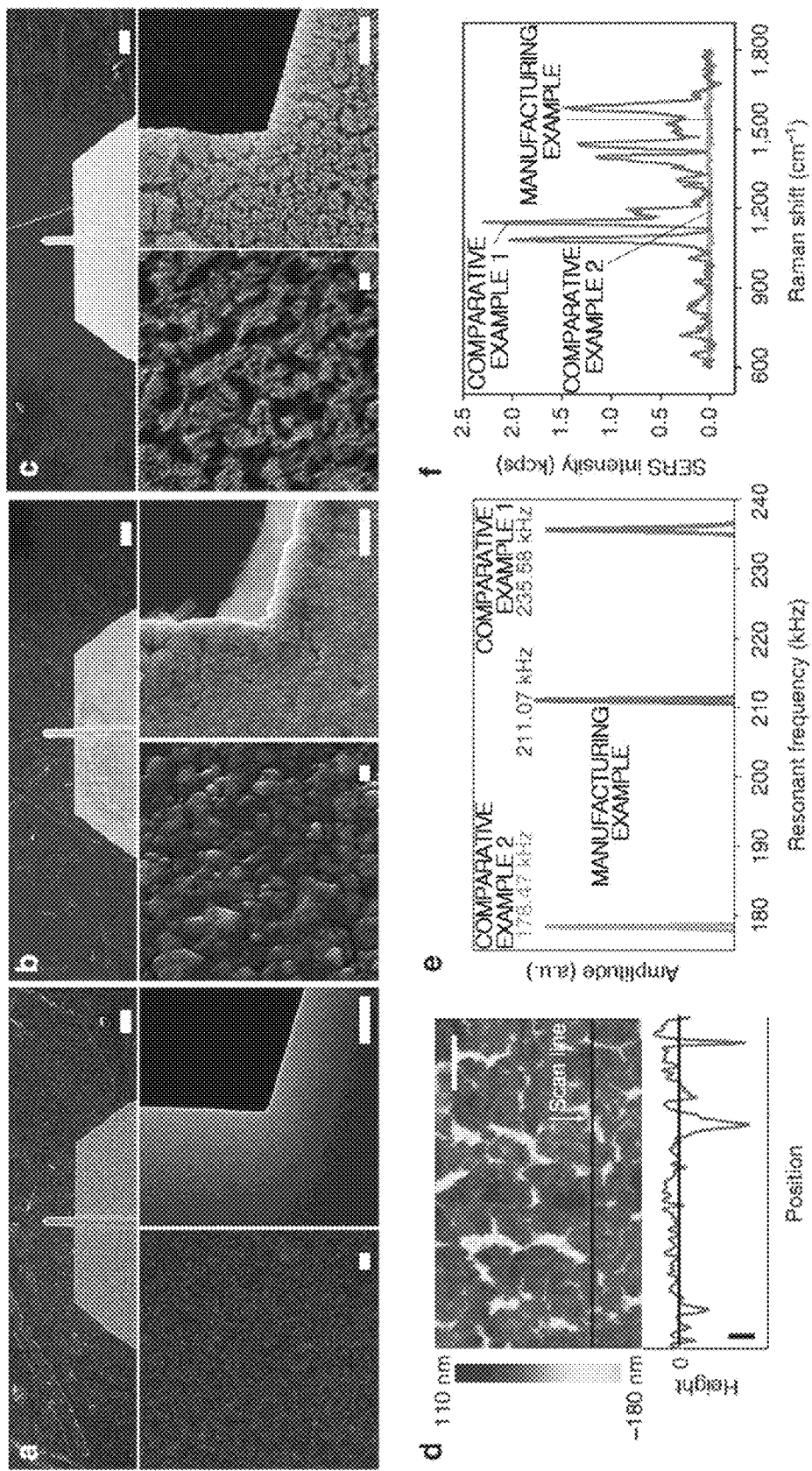
FIG. 3a is a scanning electron microscope (SEM) image of a conventional cantilever according to Comparative example 1.
FIG. 3b is an SEM image of an Au/Ag alloy layer-deposited cantilever according to Comparative example 2.
FIG. 3c is an SEM image of a nanoporous cantilever with an Au nanoporous structure (Au: 12.5 at %) according to a manufacturing example (scale bar: 100 μm at top, 1 μm at right bottom, 100 nm at left bottom).
FIG. 3d shows a tapping mode atomic force microscope (tmAFM) image and analysis of a resonator according to a manufacturing example (scale bar: 500 nm each at top and bottom).
FIG. 3e shows resonant frequencies of resonators according to Comparative examples 1 and 2 and a manufacturing example.
FIG. 3f shows surface-enhanced Raman scattering (SERS) signals of resonators according to Comparative examples 1 and 2 and a manufacturing example from p-aminothiophenol (p-ATP).

As shown in FIG. 3e, the resonant frequency of Comparative example 2 was greatly reduced when compared to Comparative example 1, which is a result of an increased mass by the nanoporous structure formed on the surface. It can be seen that the resonant frequency of the manufacturing example obtained by etching Comparative example 2 is higher than that of Comparative example 2 due to silver removal, but is lower than that of Comparative example 1 due to the nanoporous structure formed on the surface.

As shown in FIG. 3f, for p-ATP molecule (100 μM), the resonators of Comparative example 1 and Comparative example 2 did not generate an SERS signal. In contrast, a Raman signal was detected in a range of 100 to 1400 cm$^{-1}$ from the resonator according to the manufacturing example of the present disclosure, and in particular, a characteristic strong Raman signal was detected in a range of 1140 to 1145 cm$^{-1}$, and it was found that it was possible to discriminate a detected molecule through this.

Figure 4:
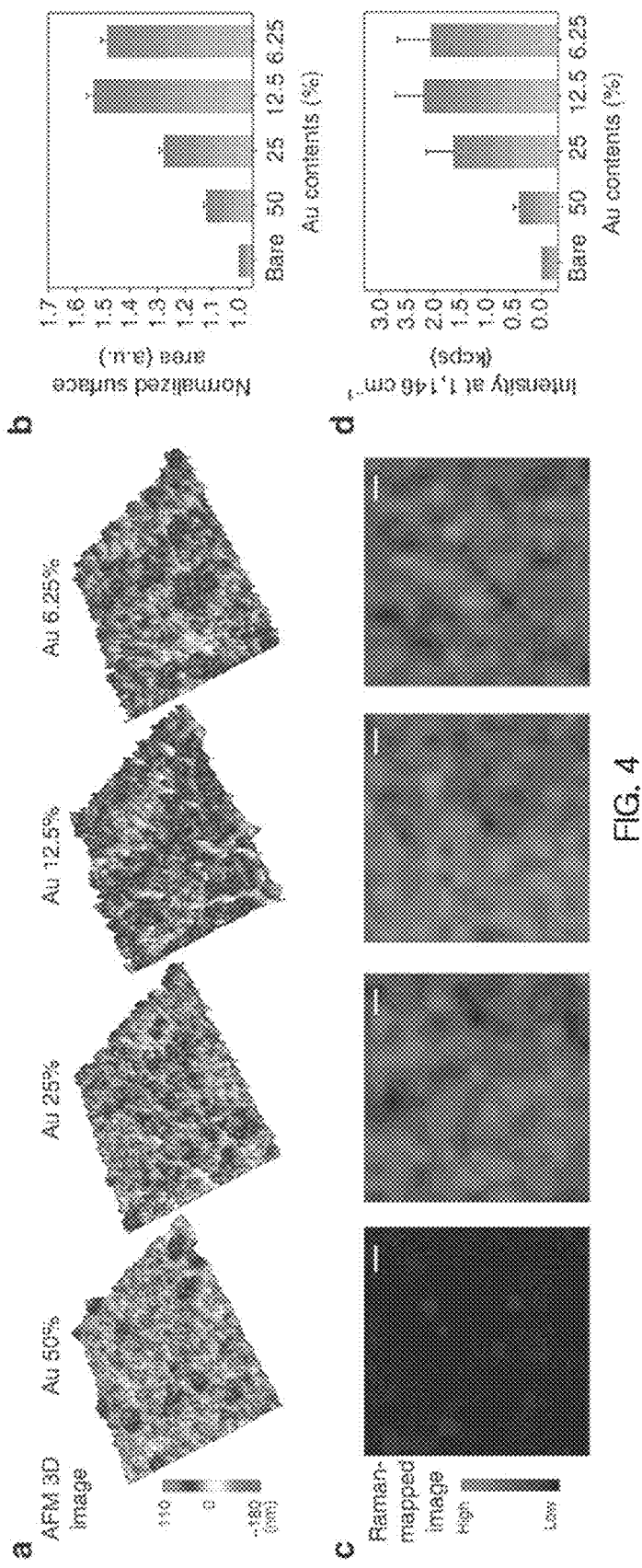
FIG. 4a is a series of 3-dimensional (3D) tmAFM images, based on Au contents, of a resonator manufactured according to a manufacturing example of the present disclosure.
FIG. 4b is its normalized surface area ratio to Comparative example 1.
FIG. 4c is a series of Raman mapping image of a manufacturing example based on Au contents.
FIG. 4d is a graph showing its SERS intensity.

FIGS. 4a and 4b are a 3D tmAFM image and a normalized surface area ratio to Comparative example 1, of a nanoporous structure (hereinafter referred to as an 'Au content-dependent nanoporous structure') manufactured by depositing an alloy deposition solution which was each prepared with Au contents of 50, 25, 12.5, and 5.25 at % in the Au/Ag alloy layer according to the manufacturing example of the present disclosure. Particularly, it could be seen that towering geometry (violet), flat geometry (green), and valley geometry (red) were evenly deployed on the surface of the nanoporous structure manufactured using the alloy deposition solution with Au content of 12.5 at %. A normalized surface area of the resonator having the nanoporous structure with the Au content of 12.5 at % increased to 1.532±0.242. Meanwhile, as the Au content increases to 10 to 20 at %, the surface area increased, but when the Au content exceeds 20 at %, an air gap reduction phenomenon occurred, resulting in a decrease in SERS intensity.

FIGS. 4c and 4d are a Raman mapping image of an Au content-dependent nanoporous structure and a graph showing SERS intensity based on Au contents. Particularly, it was found that a signal of high intensity was generated from a nanoporous structure manufactured using an alloy deposition solution with an Au content of 12.5 at %. When the Au content is between 25 and 50 at %, a weaker Raman signal than that of a lower Au content was generated, which it was found to be caused by a lack of plasmon hot spot.

Figure 5:
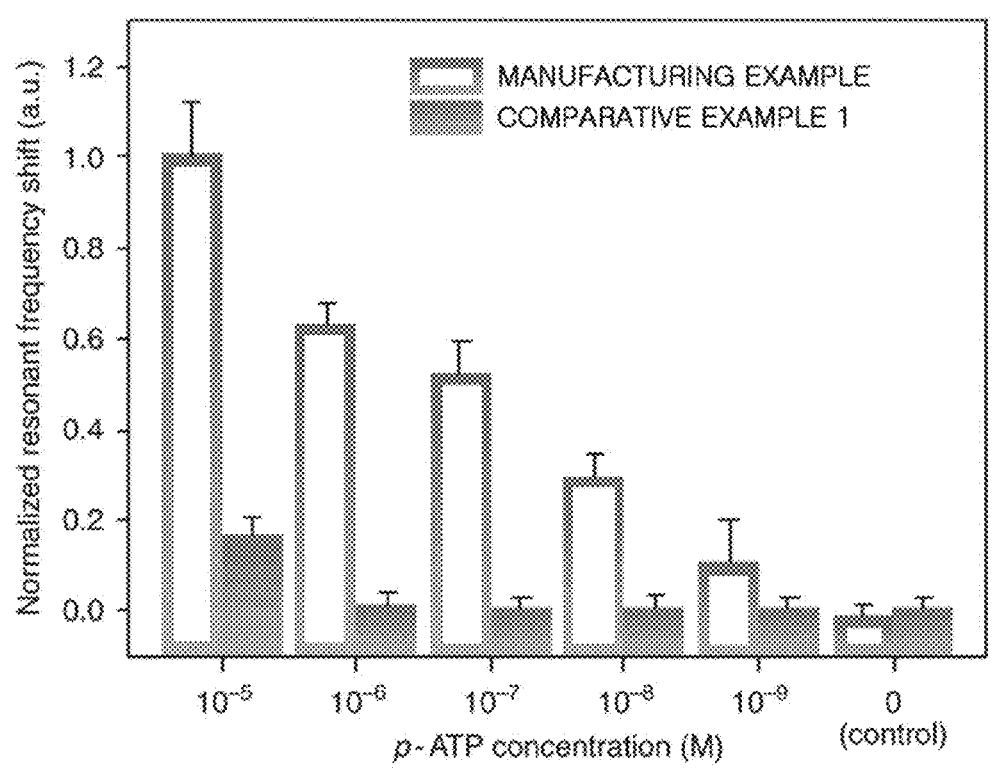
FIG. 5 is a graph showing a comparison of normalized frequency shifts of p-ATP at various concentrations using resonators according to Comparative example 1 and a manufacturing example of the present disclosure.

To conduct a quantitative analysis of molecule detection capability using the resonator according to the manufacturing example of the present disclosure, changes in resonant frequency were compared using p-ATP at various concentrations and plotted in FIG. 5.

A normalized resonant frequency may be represented by the following equation (2).

$$W_m = (\omega_c - \omega_n)/\omega_b \times 100 \qquad \text{Equation (2)}$$

In the above equation (2), $\omega_c$ denotes a resonant frequency of a molecule detected using a resonator, $\omega_n$ denotes a resonant frequency of the manufacturing example, and $\omega_b$ denotes a resonant frequency of Comparative example.

Referring to FIG. 5, Comparative example 1 showed the limit of detection of 10 μM ($10^{-5}$ M, 0.167±0.03). In contrast, the manufacturing example according to the present disclosure showed the limit of detection of 1 nM ($10^{-9}$ M, 0.110±0.091), which it was found that the limit of detection increased 10,000 times or higher.

Meanwhile, in the case of mass amplification using a sandwich technique, for example, the limit of detection may be more greatly increased. For amplification, p-ATP bonded PEG was synthesized using an amine-NHS carboxylate-based method, and using this, a normalized resonant frequency shift was measured and plotted in FIG. 6. p-ATP bonded PEG was manufactured by causing a reaction of p-aminothiophenol (p-ATP) and monomethoxy-NHS-activated PEG (mPEG-NHS; MW: 5 k) in a chloroform solution at room temperature for 24 hours, and removing unreacted p-ATP by dialysis (MWCO: 1 k).

Figure 6:
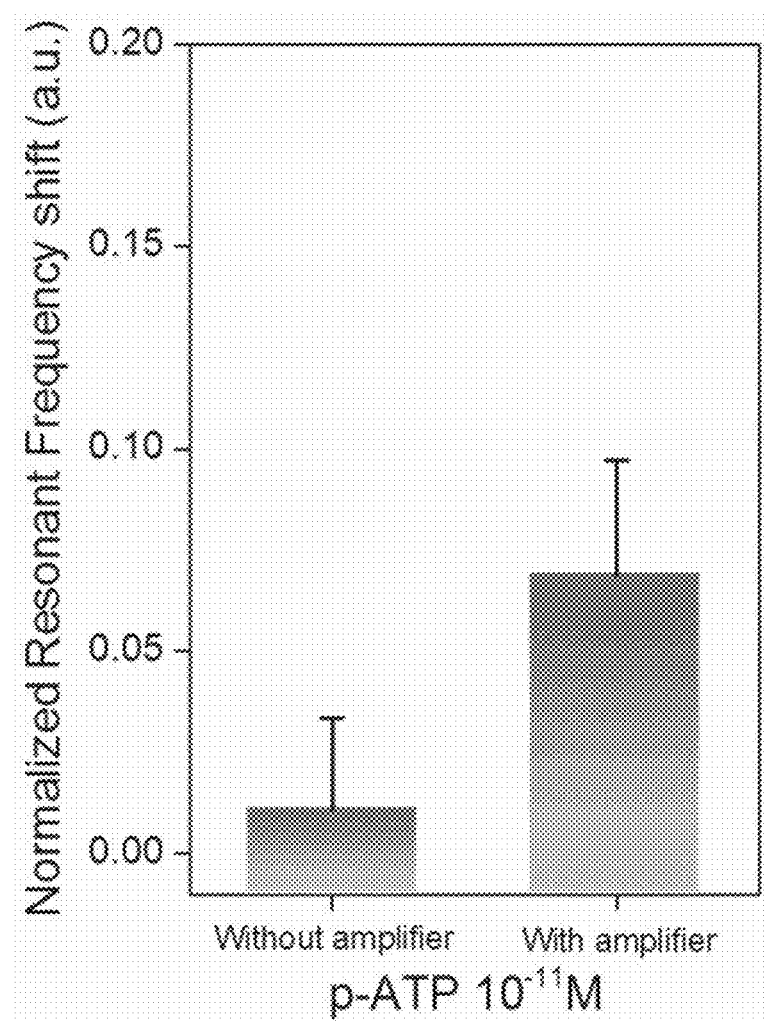
FIG. 6 is a graph showing a comparison of normalized frequency shifts with and without mass amplification of a detected molecule using a resonator according to a manufacturing example of the present disclosure.

Referring to FIG. 6, it was found that in the case of mass amplification by PEG binding, sensitivity was further improved and the limit of detection was improved to 10 pM ($10^{-11}$ M) 100 times or higher. Through the above result, it is expected that the limit of detection will be further improved using other mass amplification method.

Figure 7:
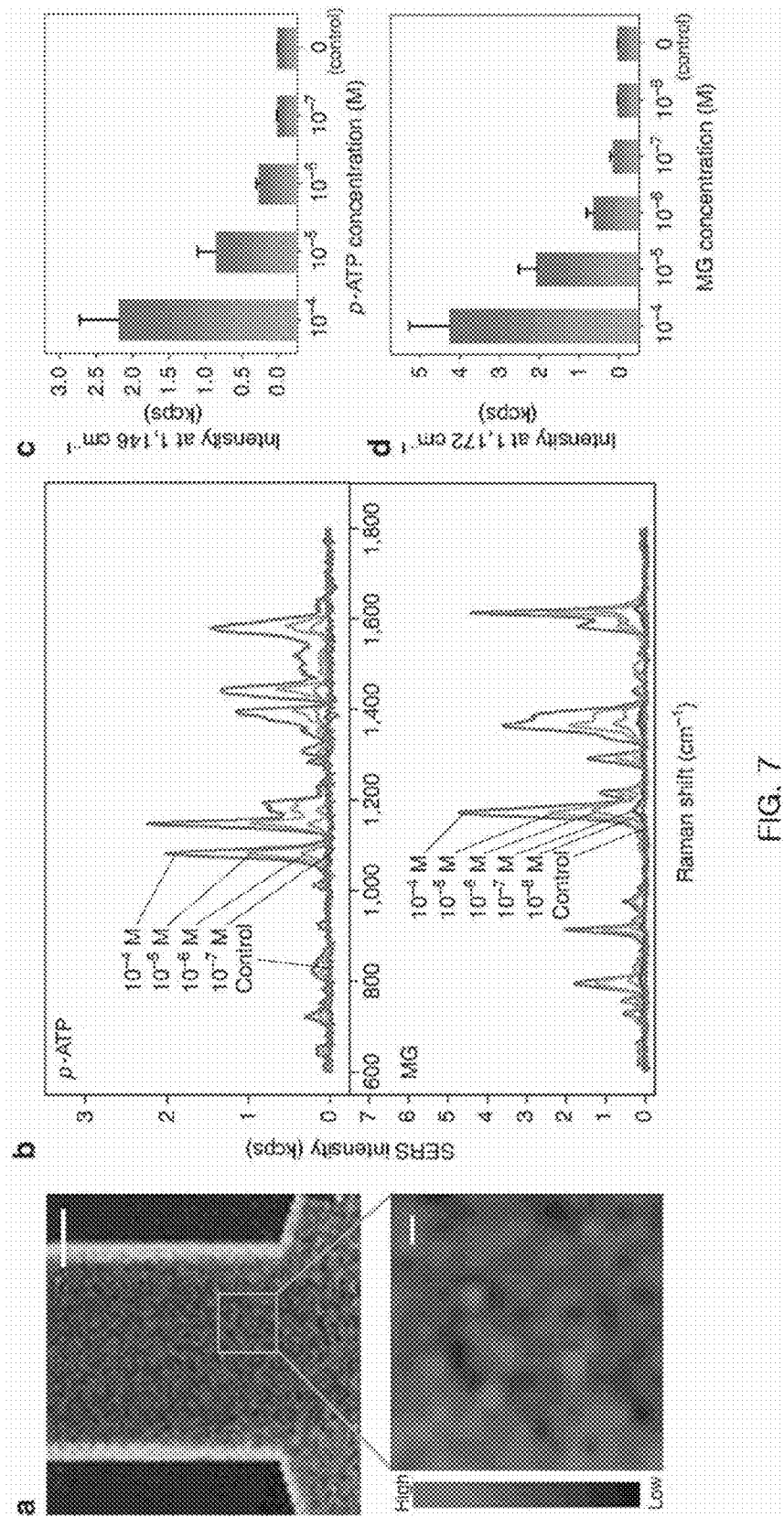
FIG. 7a shows an SEM image (top, scale bar: 10 μm) and a Raman mapping image (bottom, scale bar: 1 μm) of a p-ATP attached resonator showing a SERS signal of a detected molecule using a resonator according to a manufacturing example of the present disclosure.
FIG. 7b shows an SERS signal measured from a detected molecule at various concentrations using each of p-ATP (top) and malachite green isothiocyanate (MG) using a resonator according to a manufacturing example of the present disclosure.
FIG. 7c is a graph showing a comparison of SERS intensity of p-ATP at various concentrations of a SERS signal of a detected molecule using a resonator according to a manufacturing example of the present disclosure.
FIG. 7d is a graph showing a comparison of SERS intensity of MG at various concentrations of a SERS signal of a detected molecule using a resonator according to a manufacturing example of the present disclosure.

SEM imaging and SERS sensing was performed on p-ATP and malachite green isothiocyanate (MG) at various concentrations using the resonator according to the manufacturing example of the present disclosure, and was plotted in FIG. 7.

Referring to FIG. 7b, a characteristic Raman scattering peak could be detected at 1079, 1140-1146, 1383, and 1436 $cm^{-1}$. Meanwhile, for quantitative analysis, intensity comparison at 1146 $cm^{-1}$ based on p-ATP concentrations and intensity comparison at 1172 $cm^{-1}$ based on MG concentrations were carried out. Through the above results, it was found that the limit of detection for p-ATP was 1 μM, and the limit of detection for MG was 100 nM. Through the above results, it was seen that the nanoporous cantilever according to the present disclosure may discriminate a molecule to be detected, and sensitivity was improved 10,000 times higher than that of a related art.

What is claimed is:

1. A nanoporous cantilever, comprising:
   a substrate in a shape of a plate;
   a tip formed at a front end of the substrate; and
   a nanoporous structure formed on the tip,
   wherein the nanoporous structure is formed by chemically etching a gold and silver alloy to remove the silver,
   wherein the gold and silver alloy contains from 12.5 to 6.25 at % gold prior to etching.

2. The nanoporous cantilever according to claim 1, wherein the nanoporous structure is a structure in which a plurality of nanopores having an average diameter of 5 to 100 nm and a plurality of nanochannels having an average diameter of 50 to 1000 nm are connected to each other in three dimensions.

3. The nanoporous cantilever according to claim 1, wherein the nanoporous structure further comprises any one metal or at least two metals selected from the group consisting of chrome, platinum, aluminum and copper.

4. The nanoporous cantilever according to claim 1, wherein the nanoporous structure has a thickness of 10 nm to 10 μm.

5. The nanoporous cantilever according to claim 1, wherein the nanoporous cantilever further comprises a piezo-electric resistance sensor.

6. The nanoporous cantilever according to claim 1, wherein the nanoporous cantilever emits a Raman scattering signal.

7. The nanoporous cantilever according to claim 1, wherein the nanoporous structure comprises a plurality of nanopores having an average diameter of 5 to 100 nm and a plurality of nanochannels having an average diameter of 50 to 1000 nm,
   wherein the one or more of the plurality of nanopores, one or more of the plurality of nanochannels, or one or more of the plurality of nanopores and the plurality of nanochannels are connected to each other.

8. A multisensor for detecting a material comprising a nanoporous cantilever according to claim 1.

9. A method for manufacturing a nanoporous cantilever, comprising:
   depositing a metal/silver alloy layer, comprising from 12.5 to 6.25 at % gold, on a tip formed at a front end of a substrate; and
   forming a metal nanoporous structure on the tip by etching the metal/silver alloy layer to selectively remove silver,
   wherein the metal optionally further comprises any one or at least two selected from chrome, platinum, aluminum and copper.

10. The method for manufacturing a nanoporous cantilever according to claim 9, wherein the nanoporous structure is a structure in which a plurality of nanopores having an average diameter of 5 to 100 nm and a plurality of nanochannels having an average diameter of 50 to 1000 nm are connected to each other in three dimensions.

11. The method for manufacturing a nanoporous cantilever according to claim 9, wherein the nanoporous structure comprises a plurality of nanopores having an average diameter of 5 to 100 nm and a plurality of nanochannels having an average diameter of 50 to 1000 nm,
   wherein the one or more of the plurality of nanopores, one or more of the plurality of nanochannels, or one or more of the plurality of nanopores and the plurality of nanochannels are connected to each other.

12. A method for detecting a material, comprising:
providing a sample; and
measuring a resonant frequency shift and a surface-enhanced Raman scattering signal from the sample using a nanoporous cantilever according claim 1.

13. The method for detecting a material according to claim 12, wherein the material is at least one selected from a chemical molecule, protein, an antibody, a virus, a bacteria, DNA, aptamer, and a low molecular biomolecule.

14. The method for detecting a material according to claim 12, wherein the resonant frequency shift and a surface-enhanced Raman scattering signal are measured simultaneously.

\* \* \* \* \*